United States Patent [19]

Tatsuoka et al.

[11] Patent Number: 5,312,625
[45] Date of Patent: May 17, 1994

[54] FUSED 7-MEMBERED CYCLIC COMPOUND AND ANTIPSYCHOTIC PREPARATION CONTAINING THE SAME

[75] Inventors: Toshio Tatsuoka, Nishinomiya; Kayoko Nomura, Takatsuki, both of Japan

[73] Assignee: Suntory Limited, Osaka, Japan

[21] Appl. No.: 60,701

[22] Filed: May 11, 1993

Related U.S. Application Data

[63] Continuation of Ser. No. 661,132, Feb. 27, 1991, abandoned.

[30] Foreign Application Priority Data

Feb. 28, 1990 [JP] Japan ..................... 2-45753
Jun. 28, 1990 [JP] Japan ..................... 2-168554

[51] Int. Cl.$^5$ ............................. A61F 13/00
[52] U.S. Cl. ..................... 424/433; 424/451; 424/461; 514/211; 514/221; 540/490; 540/511
[58] Field of Search ........... 540/490, 511; 514/211, 514/221; 424/433, 451, 461

[56] References Cited

U.S. PATENT DOCUMENTS

| | | | |
|---|---|---|---|
| 3,898,214 | 8/1975 | Vogt | 260/239.3 |
| 4,080,449 | 3/1978 | Croisier et al. | 424/244 |
| 4,123,430 | 10/1978 | Ellefson et al. | 540/517 |
| 5,001,130 | 3/1991 | Neco et al. | 544/295 |

FOREIGN PATENT DOCUMENTS

| | | |
|---|---|---|
| 2216555 | 4/1987 | European Pat. Off. . |
| 2905637 | 8/1979 | Fed. Rep. of Germany . |
| 0127367 | 10/1981 | Japan . |
| 0130575 | 7/1985 | Japan . |
| 1-249769 | 10/1989 | Japan . |

OTHER PUBLICATIONS

Grant and Hack's Chemical Dictionary, p. 299 (1987).
Abstract of J01249769A (1989).
Drug evaluation 6th edition, pp. 111–130 (1986) (American Medical Association).
Laszlo et al., Chem. Abstracts 111, No. 97194 n (1989).
Bagoline et al., Chem. Abstracts 88, No. 145961 n (1978).
Voronkov et al., Chem. Abstracts 95, No. 168491 w (1989).
Graham, et al., Chem. Abstracts 110, No. 211845 g (1989).

Primary Examiner—Thurman K. Page
Assistant Examiner—Jyothsna Venkat
Attorney, Agent, or Firm—Burns, Doane, Swecker & Mathis

[57] ABSTRACT

A therapeutically effective antipsychotic preparation comprising a fused cyclic compound for the treatment of diseases involving the serotonergic pathway having the formula (I) or salts thereof:

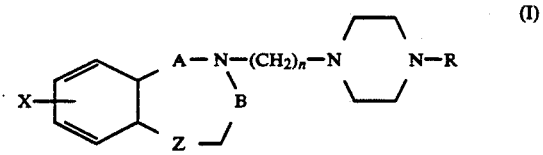

wherein both of A and B are carbonyl groups, or one represents a methylene group and the other a carbonyl group, Z represents a sulfur atom, or a nitrogen atom which may be substituted, or a methylene group, R represents an aromatic or heterocylcic group, which may be substituted, X represents a hydrogen atom, a halogen atom, a $C_1$–$C_5$ lower alkyl group, a $C_1$–$C_5$ lower alkoxy group, a $C_7$–$C_9$ arylalkoxy group, a $C_1$–$C_5$ lower acyloxy group, a $C_7$–$C_{10}$ arylcarbonyloxy group, a hydroxy group, a nitro group or an ester group, and n is an integer of 2 to 10.

28 Claims, No Drawings

FUSED 7-MEMBERED CYCLIC COMPOUND AND ANTIPSYCHOTIC PREPARATION CONTAINING THE SAME

This application is a continuation of application Ser. No. 07/661,132, filed Feb. 27, 1991, now abandoned.

BACKGROUND OF THE INVENTION

1. Field of the Invention

The present invention relates to a novel fused 7-membered cyclic compound and an antipsychotic preparation containing the same.

The novel fused 7-membered cyclic compound and salts thereof according to the present invention have a potent affinity for the serotonin receptor, and are useful as a therapeutic for diseases involving the serotonergic pathway, including psychonervous diseases such as anxiety neurosis, phobia, obsessive compulsive neurosis, stress disorder after mental trauma, and depression neurosis as well as food intake disorders, climacteric disorders, and infantile autism.

2. Description of the Related Art

In the prior art, benzodiazepine type drugs, antipsychotics, and antidepressants have been used as the therapeutics for anxiety neurosis, phobia and obsessive-compulsive neurosis, but such drugs have problems of effectiveness and side effects.

Particularly for anxiety neurosis, although benzodiazepine type drugs are currently used, a narcotic action, muscle relaxation and a further dependency occur, and therefore there is a need to develop a specific antianxiety drug without these side effects.

In recent years, various attempts have been made to solve these various problems, and among them, drugs having an affinity selectively for the $5HT_{1A}$ subtype of serotonin receptors have been considered as possibilities for use as an antianxiety drug; Buspirone, Gepirone, and Ipsapirone have been or are being developed.

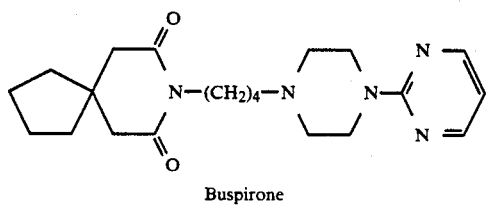

Buspirone

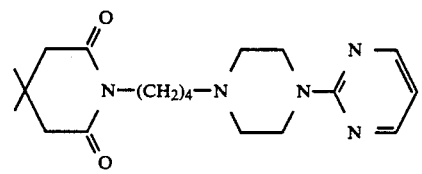

Gepirone

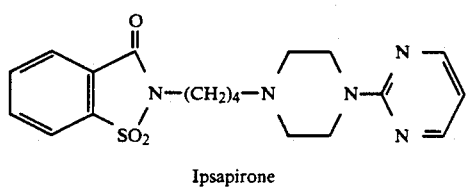

Ipsapirone

Buspirone, Gepirone, and Ipsapirone as mentioned above partially alleviate various side effects, compared with the benzodiazepine drugs of the prior art, but are not satisfactory, and thus there is a strong need to develop antianxiety drugs with less side effects and a higher specificity.

SUMMARY OF THE INVENTION

Accordingly, the objects of the present invention are to eliminate the above-mentioned disadvantages of the prior art and to provide a novel compound having a higher selectivity and more potent affinity for a $5HT_{1A}$ receptor, and having an antipsychotic effect.

Other objects and advantages of the present invention will be apparent from the following description.

In accordance with the present invention, there is provided a fused cyclic compound having the formula (I) or salts thereof:

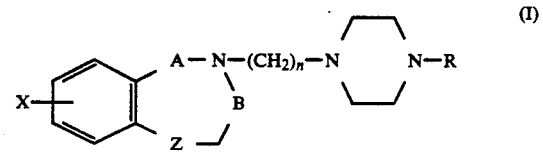

wherein both of A and B are carbonyl groups, or one represents a methylene group and the other a carbonyl group, Z represents a sulfur atom, or a nitrogen atom which may be substituted, or a methylene group, R represents an aromatic or heterocyclic group, which may be substituted, X represents a hydrogen atom, a halogen atom (preferably chlorine, bromine, fluorine), a $C_1$-$C_5$ lower alkyl group (preferably $C_1$-$C_3$ lower alkyl group), a $C_1$-$C_5$ lower alkoxy group (preferably $C_1$-$C_3$ alkoxy group), a $C_7$-$C_9$ arylalkoxy group (preferably a phenylalkoxy group), a $C_1$-$C_5$ lower acyloxy group (preferably) a $C_1$-$C_3$ lower acyloxy group), a $C_7$-$C_{10}$ arylcarbonyloxy group (preferably a $C_7$-$C_8$ arylcarbonyloxy group), a hydroxy group, a nitro group or an ester group (preferably a $C_1$-$C_3$ lower alkyl ester group), and n is an integer of 2 to 10, preferably 2 to 8, more preferably 2 to 5, which is effective as an active ingredient for an antipsychotic preparation.

In accordance with the present invention, there is also provided a fused cyclic compound having the formula (II), and salts thereof:

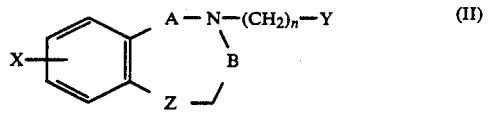

wherein both of A and B are carbonyl groups, or one represents a methylene group and the other a carbonyl group, Z represents a sulfur atom, or a nitrogen atom which may be substituted, or a methylene group, X represents a hydrogen atom, a halogen atom (preferably chlorine, bromine, fluorine), a $C_1$-$C_5$ lower alkyl group (preferably $C_1$-$C_3$ lower alkyl group), a $C_1$-$C_5$ lower alkoxy group (preferably $C_1$-$C_3$ alkoxy group), a $C_7$-$C_9$ arylalkoxy group (preferably a phenylalkoxy group), a $C_1$-$C_5$ lower acyloxy group (preferably a $C_1$-$C_3$ lower acyloxy groups, a $C_7$-$C_{10}$ arylcarbonyloxy group (preferably a $C_7$-$C_8$ arylcarbonyloxy group), a hydroxy group, a nitro group or an ester group (preferably a $C_1$-$C_3$ lower alkyl ester group), Y represents a halogen atom, and n is an integer of 2 to 10, preferably 2 to 8, more preferably 2 to 5. This compound is useful as the synthetic intermediate of the above-mentioned compound having the formula (I).

DESCRIPTION OF THE PREFERRED EMBODIMENT

The compound of the formula (I) according to the present invention can be prepared as follows.

Synthesis of intermediate compound (II)

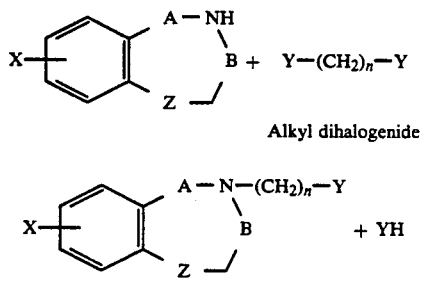

Alkyl dihalogenide

Synthesis of the final compound (I) from the intermediate compound (II)

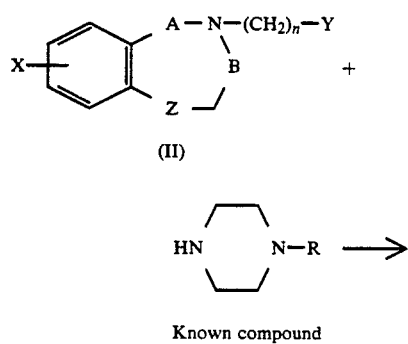

More specifically, in the compounds having the above formula (I), the compound having the following formula (Ia), wherein A is a carbonyl group, B is a methylene group and Z is a sulfur atom,

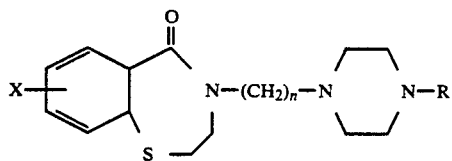

can be synthesized by reacting a compound (III) having the structure shown below and obtained by a method analogous to that described in G. S. Sidhu, G. Thyagarajan and U. T. Bhalerao, J. Chem. Soc. (C), 969 (1966) to react with a dibromoalkane:

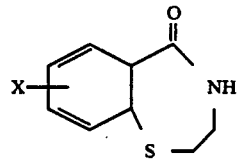

to obtain a compound (IV) having the structure shown below:

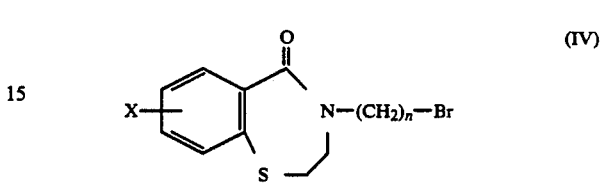

and then condensing the compound with a piperazine derivative in a conventional manner.

In the compounds having the above-mentioned formula (I), the compound (Ib) having the formula (Ib) shown below, wherein A is a methylene group, B is a carbonyl group and Z is a sulfur atom,

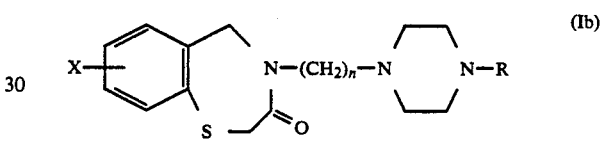

can be synthesized by allowing a compound (V) having the formula shown below and obtained by a method analogous to that described in Kost. A. N., Stankevicius, A.: Khim. Geterotsiki. Soedin., 7 (9), 1288 (1971) to react with a dibromoalkane, to obtain a compound (VI) having the structure shown below, followed by condensation with a piperazine derivative:

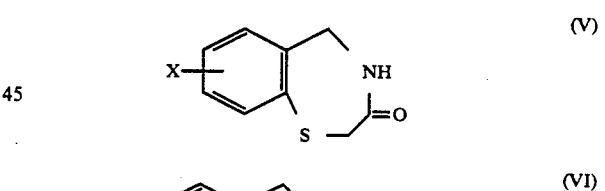

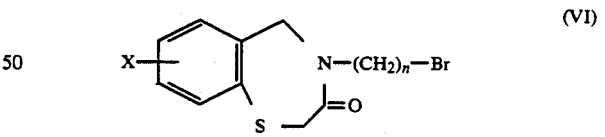

Further, in the compounds represented by the above-mentioned formula (I), the compound having the formula (Ic), wherein A and B are both carbonyls and Z is a sulfur atom,

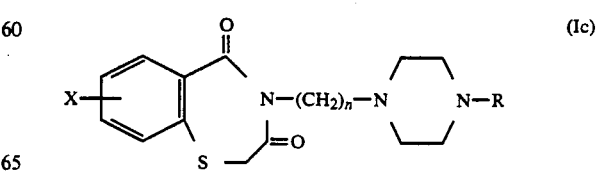

can be synthesized by allowing a compound (VII) obtained according to a method analogous to that described in A. Cattaneo, P. Galimberti, M. Melandri, Boll. Chim.—Farm., 102 541 (1963):

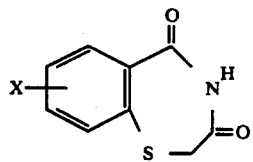
(VII)

to react with dibromoalkane to obtain a compound (VIII) having the following structure:

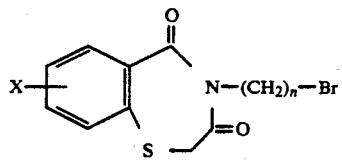
(VIII)

followed by condensation with a piperazine derivative.

In the 7-membered cyclic compounds of the above-mentioned formula (I) according to the present invention, R represents an aromatic group and a heterocyclic group, which may be also substituted as mentioned above. As such aromatic groups, there may be included $C_6$-$C_{10}$ aromatic groups, specifically phenyl groups, naphthyl groups and these aromatic groups may be also substituted with, for example, halogen atoms, (e.g., chlorine, bromine, fluorine), hydroxy group, $C_1$-$C_6$ lower alkyl groups, $C_1$-$C_5$ alkoxy groups, arylalkoxy groups, nitro groups, amino groups, $C_1$-$C_5$ amide groups, cyano groups, and ester groups (e.g., COO—$C_1$-$C_5$ lower alkyl group).

On the other hand, the preferable heterocyclic groups are rings containing 1 to 3 nitrogen atoms as well as carbon and hydrogen atoms and containing 1 to 3 unsaturated bonds in the 5 to 7-membered ring, specifically the pyridyl group, pyrimidinyl group, pyrazinyl group, pyridazinyl group and imidazolyl group, and these heterocyclic groups may be substituted with the substituents as mentioned above.

The novel fused 7-membered cyclic compound represented by the above-mentioned formula (I) of the present invention, and pharmacologically acceptable salts thereof (e.g., hydrochloride, nitrate, sulfate, hydrobromide, phosphate, methanesulfonate, p-toluenesulfonate, acetate, oxalate, malonate, succinate, tartrate, maleate, fumarate, lactate, citrate, and malate) may be administered individually per se, but can be administered, if desired or necessary, orally or parenterally in a desired dosage form (e.g., tablet, capsule, powder, liquid, injection, suppository) as a mixture with a pharmacologically acceptable carrier, excipient, and vehicle. Examples of such a carrier or vehicle include polyvinyl pyrrolidone, gum arabic, gelatin, sorbitol, cyclodextrin, tragacanth, magnesium stearate, talc, polyethylene glycol, polyvinyl alcohol, silica, lactose, crystalline cellulose, sugar, starch, calcium phosphate, vegetable oil, carboxymethyl cellulose calcium, sodium laurylsulfate, water, ethanol, glycerine, mannitol and syrup. The concentration of the compound of the formula (I) in such a pharmaceutical preparation is not particularly limited, but is preferably about 1 to 100% by weight, more preferably about 10 to 100% by weight, in the preparation. The dose also is not particularly limited, but is preferably 0.1 to 1000 mg/day/person, more preferably 1 to 500 mg/day/person, with the dose administration being generally once to 4 times per day.

EXAMPLES

The present invention is described in more detail with reference to Synthesis Examples of intermediates and Synthesis Examples and Test Examples of the compounds of the present invention, but the present invention is not limited to these Examples.

EXAMPLE 1

Synthesis of 1,3-benzothioxane-2,4-dione

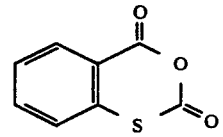

To 10 g of thiosalicylic acid were added 500 ml of benzene and 10.5 g (1 equivalent) of carboxyldiimidazole, the mixture was heated under reflux for 3 hours, benzene was evaporated, and the residue was suspended in methylene chloride and filtered through Celite. The filtrate was concentrated and developed with hexane-ethyl acetate (9:1) by silica gel column chromatography to obtain 1.91 g of the desired compound (yield 16.4%).

EXAMPLE 2

Synthesis of thiosalicylamide

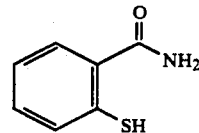

An amount of 1.94 g of the compound of Example 1 was dissolved in 50 ml of ammonia saturated methanol, the solution was stirred at room temperature for 20 minutes, the methanol was evaporated, and an aqueous citric acid solution added followed by an extraction with ethyl acetate. After washing with aqueous sodium chloride, the mixture was dried over anhydrous magnesium sulfate, the ethyl acetate solution was concentrated, and the residue developed with methylene chloridemethanol (97:3) by silica gel column chromatography to obtain 1.63 g of the desired compound (yield 99.0%).

EXAMPLE 3

Synthesis of 2-ethoxycarbonylmethylthiobenzamide

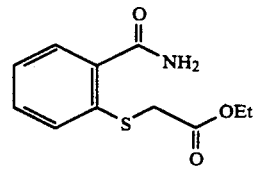

An amount of 1.72 g of the compound of Example 2 was dissolved in 50 ml of dimethylformamide, and 3.10 g of potassium carbonate (2 equivalents) and 1.50 ml of ethyl bromoacetate (1.2 equivalents) were added to the solution, the mixture was stirred under heating at 90° C.

for one hour, the reaction mixture was cooled to room temperature and then filtered, and the filtrate was concentrated. The concentrate was diluted with water and extracted with methylene chloride. After washing with aqueous sodium chloride, the mixture was dried over anhydrous magnesium sulfate, followed by evaporation of the solvent. The residue was developed with methylene chloride-methanol (97:3) by silica gel column chromatography to obtain 2.25 g of the desired compound (yield 83.4%)

EXAMPLE 4

Synthesis of 2,3,4,5-tetrahydro-1,4-benzothiazeoine-3,5-dione

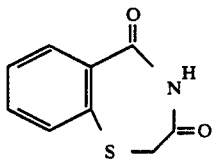 (VII)

An amount of 1.01 g of the compound of Example 3 was dissolved in 50 ml of dioxane, the solution was heated to 100° C. and 202 mg (1.2 equivalent) of 60% sodium hydride was added, followed by stirring under heating at 100° C. for 20 minutes. The reaction mixture was poured into ice-water, to which citric acid was added, and the mixture extracted with ethyl acetate. After washing with aqueous sodium chloride, the mixture was dried over anhydrous magnesium sulfate and the solvent was evaporated. The residue was developed with hexane-ethyl acetate (2:1) by silica gel column chromatography to obtain 328 mg of the desired compound (yield 40.5%)

EXAMPLE 5

Synthesis of 2-ethoxycarbonylmethylaminobenzamide

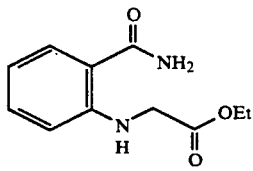

To 2 g of ortho-aminobenzamide were added 4.04 g (2 equivalents) of potassium carbonate, 4.94 g (2 equivalents) of ethyl bromoacetate, and the mixture was stirred under heating at 160° C. for 3 hours. After cooling to room temperature, water was added and the mixture extracted with ethyl acetate. After washing with aqueous sodium chloride, the mixture was dried over anhydrous magnesium sulfate, followed by evaporation of the solvent. The residue was developed with hexaneethyl acetate (1:2) by silica gel column chromatography to obtain 760 mg of the desired compound (yield 23.3%).

EXAMPLE 6

Synthesis of 2,3,4,5-tetrahydro-1,4-benzodiazeoine-3,5-dione

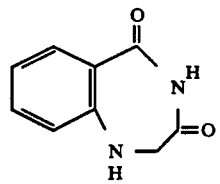

An amount of 727 mg of the compound of Example 5 was dissolved in 30 ml of dioxane, and 157 mg (1.2 equivalents) of 60% sodium hydride was added, followed by heating under reflux for 1.5 hours. The mixture was added to ice-water to which citric acid was added, and sodium hydrogen carbonate was added to make it alkaline, followed by extraction with ethyl acetate. After washing with aqueous sodium chloride, the mixture was dried over anhydrous magnesium sulfate and the solvent was evaporated. The residue was crystallized from hexane-ethyl acetate to obtain 204 mg of the desired compound (yield 35.4%)

EXAMPLE 7

Synthesis of methyl N-ethoxycarbonylmethyl-N-methylanthranylate

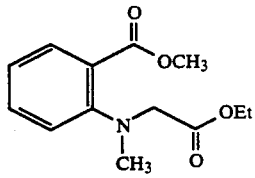

To 10 g of methyl N-methylanthranylate were added 16.7 g (2 equivalents) of potassium carbonate, 10.1 ml (1.5 equivalents) of ethyl bromoacetate, and the mixture was stirred under heating at 160° C. for 3 hours. After cooling to room temperature, ice-water was added and the mixture extracted with ethyl acetate. After washing with aqueous sodium chloride, the mixture was dried over anhydrous magnesium sulfate and the solvent evaporated. The residue was developed with hexane-ethyl acetate (9:1) by silica gel column chromatography to obtain 1.39 g of the desired compound (yield 9.1%).

EXAMPLE 8

Synthesis of methyl N-carbamylmethyl-N-methylanthranylate

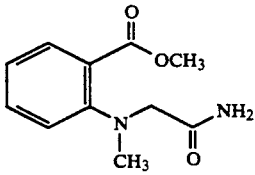

To 1.39 g of the compound of Example 7 were added 30 ml of 28% ammonia water, 30 ml of dioxane, 400 mg of ammonium chloride, and the mixture was stirred at room temperature for 48 hours. Dioxane was evaporated, and the residue extracted with methylene chloride. After washing with aqueous sodium chloride, the mixture was dried over anhydrous magnesium sulfate, and the solvent evaporated. The residue was developed with hexane-ethyl acetate (1:2) by silica gel column chromatography to obtain 232 mg of the desired compound (yield 18.9%).

EXAMPLE 9

Synthesis of 2,3,4,5-tetrahydro-1-methyl-1,4-benzodiazeoine-3,5-dione

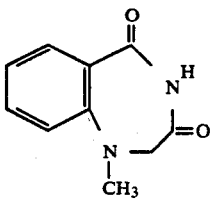

An amount of 228 mg of the compound of Example 8 was dissolved in 35 ml of dioxane, 49.3 mg (1.2 equivalents) of 60% sodium hydride added and the mixture was stirred under heating at 100° C. for 10 minutes. After cooling to room temperature, the mixture was poured into ice-water in which citric acid was added, sodium hydrogen carbonate added to make it alkaline, followed by ethyl acetate. After washing with aqueous sodium chloride, the mixture was dried over anhydrous magnesium sulfate, followed by evaporation of the solvent. The residue was crystallized from hexane-ethyl acetate to obtain 136 mg of the desired compound (yield 69.6%).

EXAMPLE 10

Synthesis of methyl 3-(2-methoxycarbonyl)phenylpropionate

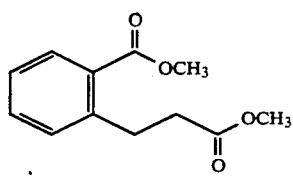

A solution of 2 g of ortho-hydroxycarbonylphenyl-propionic acid dissolved in 10 ml of methanol, heated under reflux with addition of 5 drops of conc. sulfuric acid for 30 minutes and then methanol was evaporated under normal pressure. Heating under reflux and evaporation were repeated 3 times. Water was added to the residue and the mixture extracted with ethyl acetate. After washing with aqueous sodium chloride, the mixture was dried over anhydrous magnesium sulfate and the solvent evaporated to obtain 2.22 g of the desired compound (yield 97.0%).

EXAMPLE 11

Synthesis of 3-(2-methoxycarbonyl)phenylpropanamide

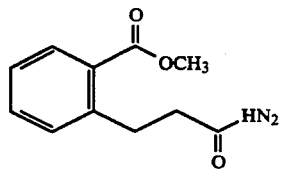

An amount of 4.36 g of the compound of Example 10 was dissolved in 120 ml of 28% ammonia water, 120 ml of dioxane, 2 g of ammonium chloride added and the mixture was stirred at room temperature for 3 weeks. Dioxane was evaporated and the residue extracted with methylene chloride. After washing with aqueous sodium chloride, the mixture was dried over anhydrous magnesium sulfate and the solvent evaporated. The residue was developed with methylene chloride-methanol (97:3) by silica gel column chromatography to obtain 1.11 g of the desired compound (yield 27.3%).

EXAMPLE 12

Synthesis of 1,3,4,5-tetrahydro-2-benzazepine-1,3-dione

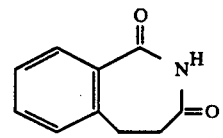

To a solution of 1.17 g of the compound of Example 11 dissolved in 60 ml of dioxane was added 271 mg (1.2 equivalents) of 60% sodium hydride, and the mixture was stirred under heating at 100° C. for 10 minutes. The reaction mixture was poured into ice-water to which citric acid was added, followed by extraction with ether. After washing with aqueous sodium chloride, the mixture was dried over anhydrous magnesium sulfate. Ether was evaporated and the precipitated crystals were filtered to obtain 866 mg of the desired compound (yield 87.5%).

EXAMPLE 13

Synthesis of 4-(4-bromobutyl)-2,3,4,5-tetrahydro-1,4-benzothiazepine-3,5-dione

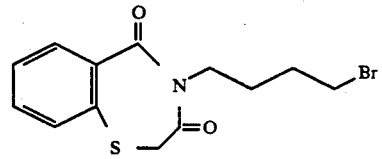

A solution of 180 mg of 2,3,4,5-tetrahydro-1,4-benzothiazepine-3,5-dione dissolved in 15 ml of dimethylformamide was ice-cooled, 0.245 ml (2 equivalents) of 1,4-dibromobutane, 48.3 mg (1.2 equivalents) 60% sodium hydride was added, followed by stirring under ice-cooling for one hour.

The reaction mixture was poured into an aqueous citric acid under ice-cooling and extracted with ether.

After washing with aqueous sodium chloride, the mixture was dried over anhydrous magnesium sulfate. The residue obtained by concentration of the ether solution was developed with hexane-ethyl acetate (6:4) by silica gel column chromatography to obtain 191 mg of the desired compound (yield 61%).

EXAMPLE 14

Synthesis of 4-(4-bromobutyl)-2,3,4,5-tetrahydro-1,4-benzodiazepine-3.5-dione

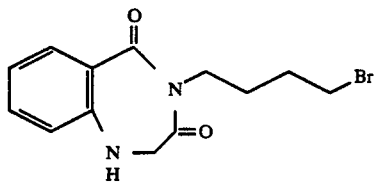

A solution of 84.2 mg of 2,3,4,5-tetrahydro-1,4-benzodiazepine-3,5-dione dissolved in 10 ml of dimethylformamide was ice-cooled, and then 0.0874 ml (1.5 equivalents) of 1,4-dibromobutane and 23.0 mg (1.2 equivalents) of 60% sodium hydride were added, followed reaction treatment and purification were conducted in the desired compound (yield 64%)

EXAMPLE 15

Synthesis of 4-(4-bromobutyl)-1-methyl-2,3,4,5-tetrahydro-1,4-benzodiazeoine-3,5-dione

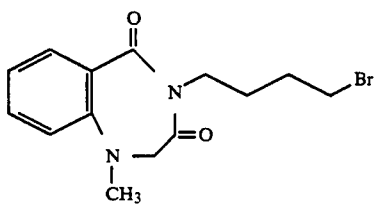

A solution of 80 mg of 1-methyl-2,3,4,5-tetrahydro-1,4-benzodiazepine-3,5-dione dissolved in 10 ml of dimethylformamide was ice-cooled, and 0.077 ml (1.5 equivalents) of 1,4-dibromobutane and 20.2 mg (1.2 equivalents) of 60% sodium hydride were added, followed by stirring under ice-cooling for 1 hour. The reaction treatment and purification were conducted in the same manner as in Example 13, to obtain 112 mg of the desired compound (yield 82%).

EXAMPLE 16

Synthesis of 2-(4-bromobutyl)-1,3,4,5-tetrahydro-2-benzazepine-1,3-dione

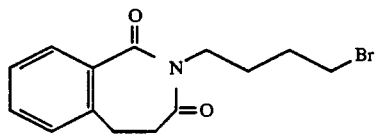

A solution of 200 mg of 1,3,4,5-tetrahydro-2-benzazepine-1,3-dione dissolved in 20 ml of dimethylformamide was ice-cooled, and then 0.209 ml (1.5 equivalents) of 1,4-dibromobutane, 54.8 mg (1.2 equivalents) of 60% sodium hydride were added, followed by stirring under ice-cooling for 1.5 hours. The reaction treatment and purification were conducted in the same manner as in Example 13, to obtain 213 mg of the desired compound (yield 60%).

EXAMPLE 17

Synthesis of 4-(4-(4-phenylpiperazinyl)butyl-2,3,4,5-tetrahydro-1,4-benzothiazepine-3,5-dione

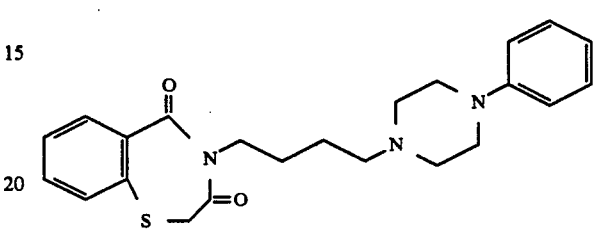

To a solution of 115 mg of compound of Example 13 dissolved in 10 ml of dioxane was added 171 mg (3 equivalents) of N-phenylpiperazine, followed by heating under reflux for 4 hours. Next, dioxane was evaporated, aqueous sodium bicarbonate added and the mixture extracted with methylene chloride. After washing the extract with aqueous sodium chloride, the mixture was dried over anhydrous magnesium sulfate. Next, the residue obtained by concentration of the methylene chloride solution was purified by silica gel column chromatography (ethyl acetate:hexane=3:1) to obtain 142 mg of the desired compound (yield 99.0%). The fumarate was obtained by converting the product to a fumarate in a conventional manner, followed by recrystallization from acetone-ether.

EXAMPLE 18

Synthesis of 4-(4-(4-(2-pyridyl)piperazinyl)butyl)-2,3,4,5-tetrahydro-1,4-benzothiazeoine-3,5-dione

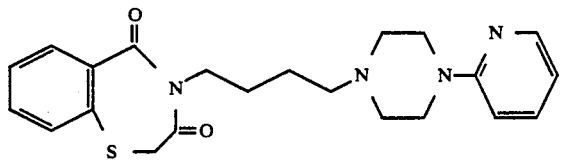

To a solution of 53.6 mg of the compound of Example 13 dissolved in 10 ml of dioxane was added 0.0796 ml (3 equivalents) of 1-(2-pyridyl)piperazine and the mixture heated under reflux for 4 hours. The product was subjected to the reaction treatment and purification in the same manner as in Example 17 to obtain the 41.7 mg (yield 62%). The maleate was obtained by converting the product to maleate in a conventional manner, followed by recrystallization from methylene chloride-ether.

EXAMPLE 19

Synthesis of 4-(4-(4-(2-pyrimidinyl)piperadinyl)butyl)-2,3,4,5-tetrahydro-1,4-benzothiazepine-3,5-dione

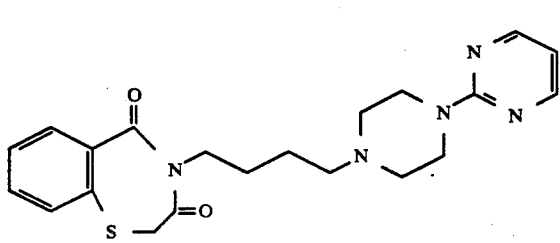

To a solution of 53.8 of the compound of Example 13 dissolved in 10 ml of dioxane was added 84.3 mg (3 equivalents) of 1-(2-pyrimidinyl)piperazine, and the mixture heated under reflux for 6 hours. The reaction treatment and purification were conducted in the same manner as in Example 17 to obtain 35.2 mg of the desired compound (yield 52%). The maleate was obtained by converting the product to maleate in a conventional manner, followed by recrystallization from methylene chloride-ether.

EXAMPLE 20

Synthesis of 4-(4-(4-phenylpiperazinyl)butyl-2,3,4,5-tetrahydro-1,4-benzodiazeoine-3,5-dione

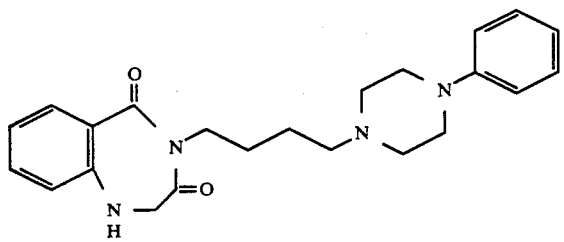

To a solution of 80 mg of the compound of Example 14 dissolved in 10 ml of dioxane was added 125 mg (3 equivalents) of N-phenylpiperazine, and the mixture heated under reflux for 4 hours. The reaction treatment and purification were conducted in the same manner as in Example 17 to obtain 98.8 mg of the desired compound (yield 98.0%). The fumarate was obtained by converting the product to fumarate, followed by recrystallization from acetone-ether.

EXAMPLE 21

Synthesis of 4-(4-(4-(2-pyridyl)piperazinyl)butyl)-2,3,4,5-tetrahydro-1,4-benzodiazepine-3,5-dione

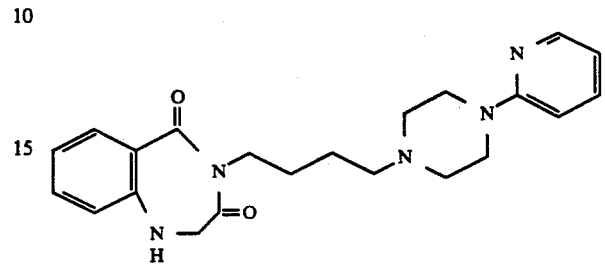

To a solution of 70 mg of the compound of Example 14 dissolved in 10 ml of dioxane was added 0.105 ml (3 equivalents) of 1-(2-pyridyl)piperazine and the mixture heated under reflux for 8 hours. The reaction treatment and purification were conducted as in Example 17, to obtain 86.2 mg of the desired compound (yield 97%). The maleate was obtained by converting the product to maleate in a conventional manner, followed by recrystallization from methylene chloride-ether.

EXAMPLE 22

Synthesis of 4-(4-(4-(2-pyrimidinyl)piperazinyl)butyl)-2,3,4,5-tetrahydro-1,4-benzodiazepine-3,5-dione To a solution of 70 mg of the compound of Example 14 dissolved in 10 ml of dioxane was added 111 mg (3 equivalents) of 1-(2-pyrimidinyl)piperazine, and the mixture heated under reflux for 8 hours. The reaction treatment and purification were conducted in the same manner as in Example 17 to obtain 77.0 mg of the desired compound (yield 87%). The maleate was obtained by converting the product to maleate, followed by recrystallization from methylene chloride-ether.

EXAMPLE 23

Synthesis of 1-methyl-4-(4-(4-phenylpiperazinyl)butyl)-2,3,4,5-tetrahydro-1,4-benzodiazepine-3.5-dione

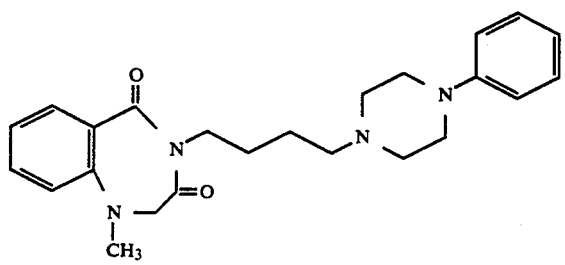

To a solution of 30 mg of the compound of Example 15 dissolved in 5 ml of dioxane was added 44.9 mg (3 equivalents) of N-phenylpiperazine, and the mixture heated under reflux for 4 hours. The reaction treatment and purification were conducted as in Example 17, to obtain 34.0 mg of the desired compound (yield 90.7%). The fumarate was obtained by converting the product to fumarate in a conventional manner, followed by recrystallization from ether.

EXAMPLE 24

Synthesis of 1-methyl-4-(4-(4-(2-pyridyl)piperazinyl)butyl)-2,3,4,5-tetrahydro-1,4-benzodiazepine-3,5-dione

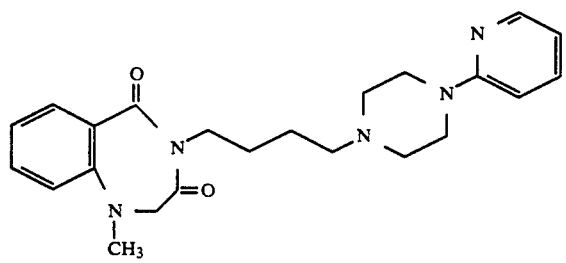

To a solution of 50.6 mg of the compound of Example 15 dissolved in 10 ml of dioxane was added 0.0725 mg (3 equivalents) of 1-(2-pyridyl)piperazine, followed by stirring under heating at 110° C. for 17 hours. The reaction treatment and purification were conducted in the same manner as in Example 17 to obtain 62.4 mg of the desired compound (yield 99%). The maleate was obtained by converting the product to maleate in a conventional manner, followed by recrystallization from methylene chloride-ether.

EXAMPLE 25

Synthesis of 1-methyl-4-(4-(4-(2-pyrimidinyl)piperadinyl)butyl-2,3,4,5-tetrahydro-1,4-benaodiazepine-3,5-dione

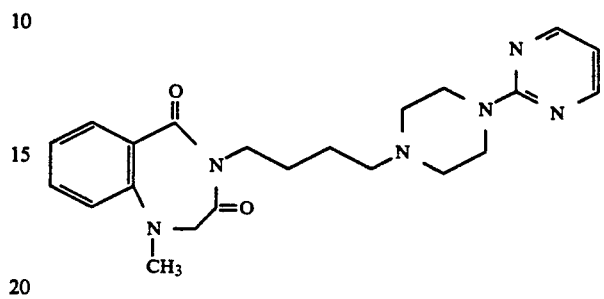

To a solution of 56.2 mg of the compound of Example 15 dissolved in 10 ml of dioxane was added 85.1 mg (3 equivalents) of 1-(2-pyrimidinyl)piperazine, followed by stirring under heating at 110° C. for 17 hours. The reaction treatment and purification were conducted in the same manner as in Example 17 to obtain 62.8 mg of the desired compound (yield 89%). The maleate was obtained by converting the product to maleate in a conventional manner, followed by recrystallization from methylene chloride-ether.

EXAMPLE 26

Synthesis of 2-(4-(4-phenylpiperazinyl)butyl)-1,3,4,5-tetrahydro-2-benzazepine-1,3-dione

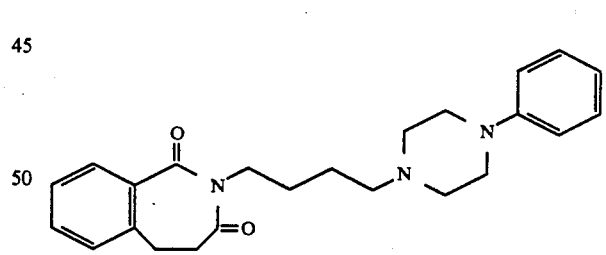

To a solution of 69.4 mg of the compound of Example 16 dissolved in 10 ml of dioxane was added 109 mg (3 equivalents) of N-phenylpiperazine, and the mixture heated under reflux for 17 hours. The reaction treatment and purification were conducted in the same manner as in Example 17 to obtain 63.5 mg of the desired compound (yield 72.5%). The fumarate was obtained by converting the product to fumarate in a conventional manner, followed by recrystallization from acetoneether.

EXAMPLE 27

Synthesis of 2-(4-(4-(2-pyridyl)piperazinyl)butyl)-1,3,4,5-tetrahydro-2-benzazepine-1,3-dione

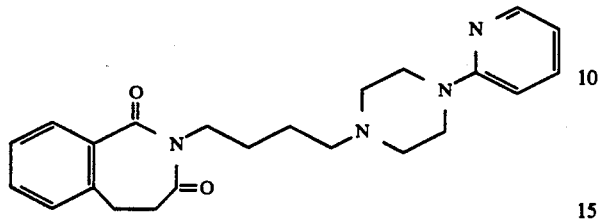

To a solution of 101 mg of the compound of Example 16 dissolved in 10 ml of dioxane was added 0.152 ml (3 equivalents) of 1-(2-pyridyl)piperazine, followed by heating under reflux for 8 hours. The reaction treatment and purification were conducted in the same manner as in Example 17 to obtain 116 mg of the desired compound (yield 91%). The maleate was obtained by converting the product to maleate in a conventional manner, followed by recrystallization from methylene chloride-ether.

EXAMPLE 28

Synthesis of 2-(4-(4-(2-pyrimidinyl)piperazinyl)butyl)-1,3,4,5-tetrahydro-2-benzazepine-1,3-dione

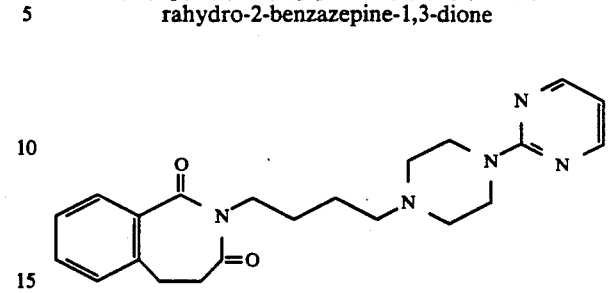

To a solution of 99.3 mg of the compound of Example 16 dissolved in 10 ml of dioxane was added 158 mg (3 equivalents) of 1-(2-pyrimidinyl)piperazine, followed by heating under reflux for 8 hours. The reaction treatment and purification were conducted similarly as in Example 17 to obtain 109 mg of the desired compound (yield 87%). The maleate was obtained by converting the product to maleate in a conventional manner, followed by recrystallization from methylene chloride-ether.

The physical data of the representative compounds obtained in the respective Examples as described above are shown in Table 1.

TABLE 1

| Example | Melting point | IR (cm$^{-1}$) | | NMR (δ ppm) | Elemental analysis |
|---|---|---|---|---|---|
| 4 | m.p. 144–145° C. | 3100 1650 1420 1345 1120 880 735 | 1705 1580 1385 1300 1040 760 | 3.62 (s, 2H), 7.45–7.58 (m, 3H), 8.18–8.24 (m, 2H) | — |
| 6 | m.p. 165–168° C. | 3340 1670 1490 1335 1270 1135 | 3180 1605 1470 1325 1250 750 | 3.94 (s, 2H), 4.49 (brs, 1H), 6.82 (d, 1H, J=7.9 Hz), 7.02 (dd, 1H, J= 7.3 Hz, 7.9 Hz), 7.40 (dd, 1H, J= 7.3 Hz 7.9 Hz), 8.14 (brs, 1H), 8.23 (d, 1H, J=7.9 Hz) | — |
| 9 | m.p. 131–133° C. | 3190 2880 1650 1435 1340 1200 1080 | 3070 1705 1505 1395 1325 1140 745 | 3.18 (s, 3H), 3.85 (s, 2H), 6.99– 7.06 (m, 2H), 7.48 (dt, 1H, J= 1.3 Hz, 7.9 Hz), 8.14 (brs, 1H), 8.27 (dd, 1H, J=1.3 Hz, 7.9 Hz) | — |
| 12 | m.p. 103–105° C. | 3180 2880 1660 1450 1350 1300 1130 790 695 | 3070 1700 1595 1370 1325 1200 855 740 | 2.88–2.92 (m, 2H), 3.09–3.13 (m, 2H), 7.23 (d, 1H, J=7.3 Hz), 7.42 (t, 1H, J=7.9 Hz), 7.52 (ddd, 1H, J=1.3 Hz, 7.3 Hz, 7.9 Hz), 8.12 (dd, 1H, J=1.3 Hz, 7.9 Hz) | — |
| 13 | Oily product | 2950 1690 1580 1355 1270 1200 1105 920 740 | 2860 1630 1430 1320 1230 1170 1080 785 690 | 1.75–1.96 (m, 4H), 3.43 (t, 2H, J= 6.2 Hz), 3.68 (s, 2H), 4.03 (t, 2H, J=6.2 Hz), 7.31–7.49 (m, 3H), 8.17– 8.20 (m, 1H) | (Calcd) 326.9927 (Found) 326.9890 |
| 14 | m.p. 60–61° C. | 3300 1690 1600 1420 1285 1120 1000 | 2850 1630 1480 1320 1150 1095 780 | 1.77–1.93 (m, 4H), 3.40 (t, 2H, J= 6.6 Hz), 3.92 (d, 2H, J=4.6 Hz), 3.93 (t, 2H, J=6.6 Hz), 4.77 (t, 1H, J=4.6 Hz), 6.79 (d, 1H, J=7.3 Hz), 6.95 (t, 1H, J=7.3 Hz), 7.35 (dt, 1H, J=1.3 Hz & 7.3 Hz), 8.25 (dd, 1H, J=1.3 Hz & 7.3 Hz) | (Calcd) 310.0316 (Found) 310.0312 |

TABLE 1-continued

| Example | Melting point | IR (cm$^{-1}$) | | NMR (δ ppm) | Elemental analysis |
|---|---|---|---|---|---|
| 15 | Oily product | 740 2950 1700 1600 1435 1375 1200 1005 750 | 695 2880 1640 1500 1395 1335 1110 780 700 | 1.74–1.96 (m, 4H), 3.22 (s, 3H), 3.41 (t, 2H, J=6.2 Hz) 3.86 (s, 2H), 3.92 (t, 2H, J=6.2 Hz), 6.94 (d, 1H, J=7.9 Hz), 6.96 (t, 1H, J=7.9 Hz), 7.45 (dt, 1H, J=1.4 Hz & 7.9 Hz), 8.32 (dd, 1H, J=1.4 Hz & 7.9 Hz) | (Calcd) 324.0473 (Found) 324.0487 |
| 16 | Oily product | 2940 1690 1595 1330 1275 1240 1105 910 750 | 2850 1645 1440 1310 1260 1180 1030 785 705 | 1.74–1.96 (m, 4H), 3.00 (s, 4H), 3.45 (t, 2H, J=6.6 Hz), 4.03 (t, 2H, J=6.6 Hz), 7.17 (d, 1H, J=7.2 Hz), 7.36 (t, 1H, J=7.2 Hz), 7.45 (dt, 1H, J=1.3 Hz & 7.2 Hz), 7.96 (dd, 1H, J=1.3 Hz & 7.2 Hz) | (Calcd) 309.0363 (Found) 309.0362 |
| 17 | m.p. 178–180° C. (Fumarate) | 2940 1695 1600 1445 1275 1230 1090 925 745 | 2815 1640 1500 1330 1260 1105 990 790 690 | 1.51–1.75 (m, 4H), 2.42 (t, 2H, J= 7.3 Hz), 2.56–2.60 (m, 4H), 3.17– 3.21 (m, 4H), 3.68 (s, 2H), 4.03 (t, 2H, J=7.3 Hz), 6.82–6.94 (m, 3H), 7.23–7.49 (m, 5H), 8.17–8.20 (m, 1H) | HCCOOH ‖ HOOCCH<br><br>      C   H   N<br>(Calcd) 61.70 5.94 7.99<br>(Found) 61.75 5.93 8.01 |
| 18 | m.p. 124–126° C. (Maleate) | 2920 1690 1585 1430 1090 920 730 | 2800 1635 1475 1320 975 765 | 1.54–1.73 (m, 4H), 2.41 (t, 2H, J= 7.6 Hz), 2.53 (t, 4H, J=5.3 Hz), 3.53 (t, 4H, J=5.3 Hz), 3.68 (s, 2H), 4.03 (t, 2H, J=7.6 Hz), 6.59– 6.65 (m, 2H), 7.34–7.50 (m, 4H), 8.16–8.20 (m, 2H) | CHCOOH ‖ . CHCOOH<br><br>      C   H   N<br>(Calcd) 59.30 5.74 10.64<br>(Found) 58.92 5.75 10.46 |
| 19 | m.p. 153–154° C. (Maleate) | 2930 1730 1655 1580 1490 1390 1300 1110 980 790 680 | 2800 1690 1635 1540 1440 1355 1255 1080 950 735 | 1.54–1.72 (m, 4H), 2.40 (t, 2H, J= 7.6 Hz), 2.47 (t, 4H, J=4.6 Hz), 3.68 (s, 2H), 3.81 (t, 4H, J= 4.6 Hz), 4.03 (t, 2H, J=7.6 Hz), 6.47 (t, 1H, J=4.6 Hz), 7.27–7.49 (m, 3H), 8.17–8.20 (m, 1H) | CHCOOH ‖ CHCOOH<br><br>      C   H   N<br>(Calcd) 56.91 5.54 13.28<br>(Found) 56.75 5.56 13.26 |
| 20 | m.p. 128–130° C. (Fumarate) | 3355 2820 1640 1495 1355 1290 1155 1020 755 | 2945 1700 1600 1430 1320 1235 1130 920 695 | 1.47–1.73 (m, 4H), 2.37–2.43 (m, 2H), 2.54–2.58 (m, 4H), 3.16–3.19 (m, 4H), 3.96–3.97 (m, 4H), 4.71 (t, 1H, J=3.8 Hz), 6.76–6.98 (m, 5H), 7.22–7.28 (m, 2H), 7.35 (dt, 1H, J= 2.0 Hz, 7.6 Hz), 8.26 (dd, 1H, J= 2.0 Hz, 7.9 Hz) | CHCOOH ‖ HOOCCH<br><br>      C   H   N<br>(Calcd) 63.77 6.34 11.02<br>(Found) 63.46 6.45 10.73 |
| 21 | m.p. 125–128° C. (Maleate) | 3320 2800 1635 1480 1360 1280 1150 1100 975 790 | 2950 1690 1590 1430 1310 1240 1120 1080 920 740 | 1.48–1.72 (m, 4H), 2.38 (t 2H, J= 7.6 Hz), 2.50 (t, 4H, J=4.9 Hz), 3.51 (t, 4H, J=4.9 Hz), 3.90 (d, 2H, J=4.6 Hz), 3.94 (t, 2H, J=7.6 Hz), 4.74 (t, 1H, J=4.6 Hz), 6.58–6.64 (m, 2H), 6.77 (d, 1H, J=7.9 Hz), 6.94 (t, 1H, J=7.9 Hz), 7.34 (dt, 1H, J=2.0 Hz & 7.6 Hz), 7.46 (dt, 1H, J=2.0 Hz & 7.6 Hz), 8.18 (dd, 1H, J=2.0 Hz & 4.6 Hz), 8.25 (dd, 1H, J=2.0 Hz & 7.9 Hz) | CHCOOH ‖  .1/2H$_2$O CHCOOH<br><br>      C   H   N<br>(Calcd) 60.22 6.22 13.51<br>(Found) 60.46 6.06 13.28 |
| 22 | m.p. 126–133° C. (Maleate) | 3250 1690 1580 1480 1385 1300 1120 790 | 2850 1630 1540 1440 1355 1250 975 740 | 1.47–1.72 (m, 4H), 2.38 (t, 2H, J= 7.3 Hz), 2.45 (t, 4H, J=5.3 Hz), 3.80 (t, 4H, J=5.3 Hz), 3.91 (d, 2H, J=4.6 Hz), 3.94 (t, 2H, J=7.3 Hz), 4.78 (t, 1H, J=4.6 Hz), 6.46 (t, 1H, J=4.6 Hz), 6.78 (d, 1H, J=8.6 Hz), 6.94 (t, 1H, J=8.6 Hz), 7.34 (dt, 1H, J=2.0 Hz & 8.6 Hz), 8.27 (dd, 1H, J=2.0 Hz & 8.6 Hz), 8.33 (d, 2H, J=4.6 Hz) | CHCOOH ‖  .1H$_2$O CHCOOH<br><br>      C   H   N<br>(Calcd) 56.81 6.10 15.90<br>(Found) 56.82 5.96 15.76 |
| 23 | m.p. 138–139° C. (Fumarate) | 2945 1700 1600 1435 | 2820 1640 1500 1390 | 1.48–1.72 (m, 4H), 2.40 (t, 2H, J= 7.3 Hz), 2.54–2.58 (m, 4H), 3.16– 3.19 (m, 4H), 3.22 (s, 3H), 3.85 (s, 2H, 3.89–3.94 (m, 2H), 6.81–6.99 | CHCOOH ‖  .1/2H$_2$O HOOCCH<br><br>      C   H   N |

TABLE 1-continued

| Example | Melting point | IR (cm$^{-1}$) | | NMR (δ ppm) | Elemental analysis | | | |
|---|---|---|---|---|---|---|---|---|
| | | 1330 | 1235 | (m, 5H), 7.22–7.28 (m, 2H), 7.43 | (Calcd) | 63.26 | 6.64 | 10.54 |
| | | 1200 | 1135 | (dt, 1H, J=1.3 Hz, 7.6 Hz), 8.32 | (Found) | 63.66 | 6.44 | 10.68 |
| | | 1110 | 1080 | (dd, 1H, J=1.3 Hz, 8.6 Hz) | | | | |
| | | 1005 | 920 | | | | | |
| | | 755 | 695 | | | | | |
| 24 | m.p. 131–132° C. (Maleate) | 2930 | 2820 | 1.50–1.67 (m, 4H), 2.39 (t, 2H, J= | CHCOOH<br>‖<br>CHCOOH | | | |
| | | 1695 | 1625 | 7.3 Hz), 2.51 (t, 4H, J=5.3 Hz), | | | | |
| | | 1595 | 1480 | 3.22 (s, 3H), 3.52 (t, 4H, J= | | C | H | N |
| | | 1430 | 1330 | 5.3 Hz), 3.85 (s, 2H), 3.92 (t, 2H, | | | | |
| | | 1310 | 1260 | J=7.3 Hz), 6.59–6.65 (m, 2H), | (Calcd) | 61.93 | 6.35 | 13.38 |
| | | 1240 | 1100 | 6.93 (d, 1H, J=8.6 Hz), 6.96 (t, | (Found) | 61.74 | 6.39 | 13.33 |
| | | 1015 | 985 | 1H, J=8.6 Hz), 7.44 (dt, 1H, J= | | | | |
| | | 970 | 920 | 2.0 Hz & 8.6 Hz), 7.46 (dt, 1H, J= | | | | |
| | | 760 | 750 | 2.0 Hz & 8.6 Hz), 8.18 (dd, 1H, J= | | | | |
| | | | | 2.0 Hz & 4.6 Hz), 8.32 (dd, 1H, J= | | | | |
| | | | | 2.0 Hz & 8.6 Hz) | | | | |
| 25 | m.p. 160–162° C. (Maleate) | 2920 | 2760 | 1.53–1.73 (m, 4H), 2.17 (s, 3H), | CHCOOH<br>‖   .1/4H$_2$O<br>CHCOOH | | | |
| | | 1695 | 1635 | 2.37 (t, 2H, J=7.6 Hz), 2.45 (t, 4H, | | | | |
| | | 1580 | 1540 | J=4.9 Hz), 3.22 (s, 2H), 3.80 (t, | | | | |
| | | 1495 | 1440 | 4H, J=4.9 Hz), 3.91 (t, 2H, J= | | C | H | N |
| | | 1390 | 1360 | 7.6 Hz), 6.48 (t, 1H, J=4.6 Hz), | (Calcd) | 59.02 | 6.19 | 15.89 |
| | | 1330 | 1305 | 6.93 (d, 1H, J=8.6 Hz), 6.95 (t, 1H, | (Found) | 59.04 | 6.19 | 15.85 |
| | | 1260 | 1195 | J=8.6 Hz), 7.44 (dt, 1H, J=1.3 Hz & | | | | |
| | | 1110 | 980 | 8.6 Hz), 8.29 (d, 2H, J=4.6 Hz), | | | | |
| | | 790 | 770 | 8.32 (dd, 1H, J=1.3 Hz & 8.6 Hz) | | | | |
| | | 745 | | | | | | |
| 26 | m.p. 177–179° C. (Fumarate) | 2945 | 2820 | 1.50–1.73 (m, 4H), 2.45 (t, 2H, J= | CHCOOH<br>‖   .H$_2$O<br>HOOCCH | | | |
| | | 1695 | 1645 | 7.3 Hz), 2.59–2.63 (m, 4H), 2.99 (s, | | | | |
| | | 1600 | 1500 | 4H), 3.19–3.23 (m, 4H), 4.00–4.05 | | | | |
| | | 1450 | 1335 | (m, 2H), 6.82–6.96 (m, 3H), 7.15– | | C | H | N |
| | | 1315 | 1275 | 7.47 (m, 5H), 7.96 (dd, 1H, J= | (Calcd) | 63.98 | 6.71 | 7.99 |
| | | 1235 | 1130 | 1.3 Hz, 7.3 Hz) | (Found) | 63.17 | 6.23 | 7.35 |
| | | 1105 | 1010 | | | | | |
| | | 995 | 925 | | | | | |
| | | 755 | 695 | | | | | |
| 27 | m.p. 95–98° C. (Maleate) | 2930 | 2800 | 1.56–1.73 (m, 4H), 2.44 (t, 2H, J= | CHCOOH<br>‖   .3H$_2$O<br>CHCOOH | | | |
| | | 1690 | 1640 | 7.3 Hz), 2.56 (t, 4H, J=4.9 Hz), | | | | |
| | | 1590 | 1480 | 2.99 (s, 4H), 3.55 (t, 4H, J= | | C | H | N |
| | | 1435 | 1310 | 4.9 Hz), 4.03 (t, 2H, J=7.3 Hz), | | | | |
| | | 1270 | 1240 | 6.60–6.66 (m, 2H), 7.17 (d, 1H, J= | (Calcd) | 57.64 | 6.81 | 9.96 |
| | | 1200 | 1160 | 7.3 Hz), 7.36 (t, 1H, J=7.3 Hz), | (Found) | 57.44 | 6.25 | 9.70 |
| | | 1120 | 1105 | 7.41–7.50 (m, 2H), 7.96 (dd, 1H, | | | | |
| | | 975 | 925 | J=1.3 Hz & 7.3 Hz), 8.18 (dd, 1H, | | | | |
| | | 770 | 750 | J=2.0 Hz & 5.3 Hz) | | | | |
| | | 725 | 705 | | | | | |
| 28 | m.p. 137–140° C. (Maleate) | 2940 | 2800 | 1.53–1.73 (m, 4H), 2.43 (t, 2H, J= | CHCOOH<br>‖<br>CHCOOH | | | |
| | | 1695 | 1640 | 7.6 Hz), 2.50 (t, 4H, J=4.9 Hz), | | | | |
| | | 1580 | 1540 | 2.99 (s, 4H), 3.83 (t, 4H, J= | | | | |
| | | 1490 | 1445 | 4.9 Hz), 4.03 (t, 2H, J=7.6 Hz), | | C | H | N |
| | | 1360 | 1305 | 6.47 (t, 1H, J=4.9 Hz), 7.16 (d, | (Calcd) | 61.28 | 6.13 | 13.75 |
| | | 1255 | 1110 | 1H, J=7.3 Hz), 7.36 (t, 1H, J= | (Found) | 61.01 | 6.26 | 13.64 |
| | | 980 | 795 | 7.3 Hz), 7.44 (dt, 1H, J=1.3 Hz & | | | | |
| | | 755 | | 7.3 Hz), 7.96 (dd, 1H, J=1.3 Hz & | | | | |
| | | | | 7.3 Hz), 8.29 (d, 2H, J=4.9 Hz) | | | | |

The compound of the present invention exhibits a strong affinity for the serotonin receptor and exhibits an antipsychotic activity, and is useful as a therapeutic for diseases involving the serotonergic pathway, including psychonervous diseases such as anxiety neurosis, phobia, obsessive-compulsive neurosis, stress disorder after mental trauma, and depression neurosis as well as food intake disorders, climacteric disorders, and infantile autism.

The pharmacological test results are described as follows.

(1) AFFINITY FOR SEROTONIN RECEPTOR

Experimental Method

The experiment was carried out according to the method of S. T. Perouka (J. Neurochem., 47, 529–540 (1986)).

To a cerebral cortex nucleated from a Wistar-strain male rat was added 50 mM Tris-HCl (pH 7.7) buffer, and the mixture was homogenized by a Polytron ®. The homogenate was centrifuged at 40,000 G for 10 minutes, and the same buffer was added to the precipitate obtained, followed by homogenization and incubation at 37° C. for 30 minutes. The suspension was again subjected to centrifugation at 40,000 G for 10 minutes, and the same buffer was added to the precipitate, followed by homogenization and a further centrifugation at 40,000 G for 10 minutes. To the final precipitate obtained was added 50 mM Tris-HCl (10 μM pargyline, 4 mM CaCl$_2$, 0.1% ascorbic acid) (pH 7.4), and the mixture was homogenized and used for the binding test. The [$^3$H]8-OHDPAT used for the binding test was 0.4 nM, with the protein amount being 0.4 to 0.6 mg/ml and the total amount 1 ml. After incubation at 25° C. for 30 minutes, the mixture was filtered by the filtration method, using the Whatman GF/B filter, and the filter was washed 3 times with 5 ml of the same buffer. To the filter was added a scintillation cocktail, followed by a measurement by a liquid scintillation counter.

TEST RESULTS

All of the compounds of the present invention have a strong affinity of a μM order or less and their receptor binding abilities are as shown in Table 2.

TABLE 2

| Compound (Example No.) | [$^3$H]-8-OH-DPAT IC$_{50}$ (nM) |
| --- | --- |
| 17 | 9.29 |
| 18 | 3.28 |
| 19 | 14.3 |
| 21 | 13.3 |
| 22 | 67.3 |
| 24 | 61.4 |
| 25 | 270 |
| 27 | 17.1 |
| 28 | 58.4 |

We claim:

1. A fused cyclic compound having the formula (I) or salts thereof:

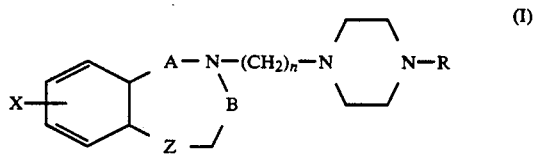

wherein both A and B are carbonyl groups, or one represents a methylene group and the other a carbonyl group, Z represents a sulfur atom, an —NH— group or an —N(CH$_3$)— group, R represents an aromatic group selected from the group consisting of phenyl and napthyl which aromatic group may be substituted with one or more groups selected from the group consisting of halogen, hydroxy, C$_1$-C$_6$ lower alkyl, C$_1$-C$_5$ alkoxy, arylalkoxy, nitro, amino, C$_1$-C$_5$ amide, cyano, and ester groups or a heterocyclic group selected from the group consisting of pyridyl, pyrimidinyl, pyrazinyl, pyridazinyl and imidazoyl groups which heterocyclic group may be substituted with one or more groups selected from the group consisting of halogen, hydroxy, C$_1$-C$_6$ lower alkyl, C$_1$-C$_5$ alkoxy, arylalkoxy, nitro, amino, C$_1$-C$_5$ amide, cyano, and ester groups, X represents a hydrogen atom, a halogen atom, a C$_1$-C$_5$ lower alkyl group, a C$_1$-C$_5$ lower alkoxy group, a C$_7$-C$_9$ arylalkoxy group, a C$_1$-C$_5$ lower acyloxy group, a C$_7$-C$_{10}$ arylcarbonyloxy group, a hydroxy group, a nitro group or an ester group, and n is an integer of 2 to 10.

2. A fused cyclic compound as claimed in claim 1, wherein A represents a carbonyl group and B represents a carbonyl or methylene group.

3. A pharmaceutical composition which is suitable for the treatment of diseases of the serotonergic pathway which comprises an amount of a compound according to claim 1, effective for the treatment of disorders involving the serotonergic pathway and a pharmaceutically acceptable carrier therefor.

4. The pharmaceutical composition of claim 3, wherein A represents a carbonyl group and B represents a carbonyl or methylene group.

5. The composition according to claim 3, wherein the composition is formulated for oral or parenteral administration.

6. The composition according to claim 5 wherein the dosage form is selected from the group consisting of a tablet, capsule, powder and a liquid.

7. The composition according to claim 4, wherein the dosage is formulated in injectable form.

8. A fused cyclic compound having the formula (II) or salts thereof:

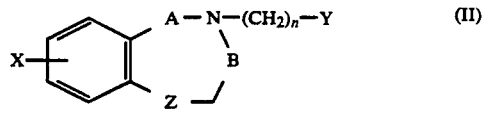

wherein both A and B are carbonyl groups, or one represents a methylene group and the other a carbonyl group, Z represents a sulfur atom, or an —NH— group or an —N(CH$_3$)— group, X represents a hydrogen atom, a halogen atom, a C$_1$-C$_5$ lower alkyl group, a C$_1$-C$_5$ lower alkoxy group, a C$_7$-C$_9$ arylalkoxy group, a C$_1$-C$_5$ lower acyloxy group, a C$_7$-C$_{10}$ arylcarbonyloxy group, a hydroxy group, a nitro group or an ester group, Y represents a halogen atom, and n is an integer of 2 to 10.

9. A composition suitable for the treatment of a disease of the serotonergic pathway which comprises an amount of a compound according to claim 8, effective for the treatment of disorders involving the serotonergic pathway and a pharmaceutically acceptable carrier therefor.

10. The composition of claim 9, wherein A represents a carbonyl group and B represents a carbonyl or methylene group.

11. The composition of claim 9, wherein the composition is formulated for oral administration.

12. The composition of claim 11, wherein the dosage form is selected from the group consisting of a tablet, capsule, powder and a liquid.

13. The composition of claim 9, wherein the composition is formulated for parenteral administration.

14. The composition according to claim 13, wherein the dosage is formulated in injectable or suppository form.

15. A method for treating a disease of the serotonergic pathway which comprises administering an effective amount of a compound according to claim 1 to a patient in need of such treatment.

16. The method according to claim 15, wherein the effective amount of the compound is 0.1 to 1000 mg/day/person.

17. The method according to claim 15, wherein the effective amount of the compound is 1 to 500 mg/day/person.

18. The method according to claim 15, wherein said effective amount of the compound is administered one to four times per day.

19. The method for treating a disease of the serotonergic pathway according to claim 15, wherein A represents a carbonyl group and B represents a carbonyl or a methylene group.

20. A method for treating a disease of the serotonergic pathway which comprises administering an effective amount of a compound according to claim 8 to a patient in need of such treatment.

21. The method according to claim 20, wherein the effective amount of the compound is 0.1 to 1000 mg/day/person.

22. The method according to claim 20, wherein the effective amount of the compound is 1 to 500 mg/day/person.

23. The method according to claim 20, wherein said effective amount of the compound is administered one to four times per day.

24. The method for treating a disease of the serotonergic pathway according to claim 20, wherein A represents a carbonyl group and B represents a carbonyl or methylene group.

25. The fused cyclic compound of claim 1 wherein R is selected from the group consisting of phenyl, pyridyl or pyrimidyl.

26. The pharmaceutical composition of claim 3 wherein R is selected from the group consisting of phenyl, pyridyl or pyrimidyl.

27. A method for treating a disease of the serotonergic pathway which comprises administering an effective amount of a compound according to claim 25 to a patient in need of such treatment.

28. A fused cyclic compound as claimed in claim 8, wherein A represents a carbonyl group and B represents a carbonyl or methylene group.

* * * * *